United States Patent [19]

Possis et al.

[11] Patent Number: 4,601,718

[45] Date of Patent: Jul. 22, 1986

[54] VASCULAR GRAFT AND BLOOD SUPPLY METHOD

[75] Inventors: Zinon C. Possis; Demetre M. Nicoloff, both of Edina, Minn.

[73] Assignee: Possis Medical, Inc., Minneapolis, Minn.

[21] Appl. No.: 630,838

[22] Filed: Jul. 13, 1984

Related U.S. Application Data

[63] Continuation-in-part of Ser. No. 489,798, Apr. 29, 1983, Pat. No. 4,562,597, which is a continuation-in-part of Ser. No. 448,955, Dec. 13, 1982, Pat. No. 4,546,499.

[30] Foreign Application Priority Data

Dec. 8, 1983 [WO] PCT Int'l Appl. .............. PCT/US83/01932

[51] Int. Cl.$^4$ ............................................. A61F 2/06
[52] U.S. Cl. .................................... 623/1; 128/334 R
[58] Field of Search ............... 3/1.4, 1.7; 128/325, 128/334 R, 334 C, 325; 623/1, 12, 66 B, 66 C

[56] References Cited

U.S. PATENT DOCUMENTS

| | | | |
|---|---|---|---|
| 2,127,903 | 8/1938 | Bowen | 623/1 |
| 3,029,819 | 4/1962 | Starks | 623/1 |
| 3,096,560 | 7/1963 | Liebig | 623/1 |
| 3,166,688 | 1/1965 | Rowand et al. | 623/1 |
| 3,490,975 | 1/1970 | Lightwood et al. | 623/1 |
| 3,570,013 | 3/1971 | Blumen | 3/1.4 |
| 3,626,947 | 12/1971 | Sparks | 623/1 |
| 3,667,069 | 6/1972 | Blackshear et al. | 623/1 |
| 3,730,186 | 5/1973 | Edmunds, Jr. et al. | 623/1 |
| 3,805,301 | 4/1974 | Liebig | 623/1 |
| 3,894,530 | 7/1975 | Dardik et al. | 623/1 |
| 3,945,052 | 3/1976 | Liebig | 623/1 |
| 3,974,526 | 8/1976 | Dardik et al. | 3/1.4 |
| 3,988,782 | 11/1976 | Dardik et al. | 623/1 |
| 4,240,794 | 12/1980 | Holman et al. | 623/1 |
| 4,321,711 | 3/1982 | Mano | 623/1 |
| 4,356,571 | 11/1982 | Esper et al. | 623/1 |

OTHER PUBLICATIONS

Hershey et al.; "Atlas of Vas. Sur."; pp. 289 and 332; 441; 1973.

Vargas et al.; "The Use of Nylon Net . . . "; Surgery, vol. 34, #6, 12/1953, pp. 1061–1075.

"The Experimental Use of Heterologous Umbilical Vein Grafts as Aortic Substitutes", *Singapore Medical Journal*, vol. 3, No. 1, Mar., 1962.

*Primary Examiner*—Richard J. Apley
*Assistant Examiner*—Gregory Beaucage
*Attorney, Agent, or Firm*—Burd, Bartz & Gutenkauf

[57] ABSTRACT

A graft is used to supply blood to one or more coronary artery branches. The graft is also usable as a peripheral revascularization and inter position prosthesis to supply blood to desired blood vessels. The graft has an elongated U-shaped tubular body providing a continuous passage for carrying blood from a high pressure blood supply to a blood receiver. One or more openings in the body allow blood to flow into the coronary artery branches. The flow and pressure of the blood in the passage is controlled by a restriction providing a restricted passage located remote from the inlet end of the tubular body. In one embodiment, the restriction is reinforced with a sleeve to maintain a desired cross sectional area and length of the restricted passage. The pressure differential between the blood supply and blood receiver maintains continuous and adequate blood flow at a desired pressure in the continuous passage and provides a continual supply of blood for the coronary artery branches.

61 Claims, 32 Drawing Figures

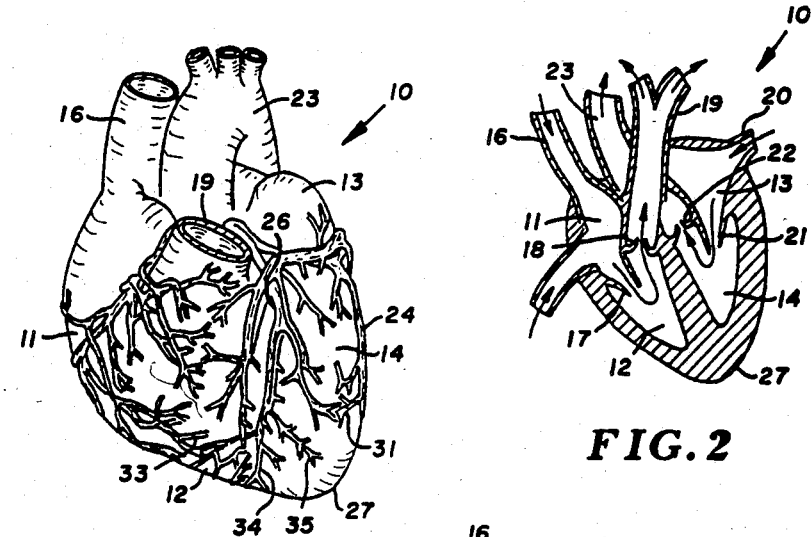
FIG. 1
FIG. 2
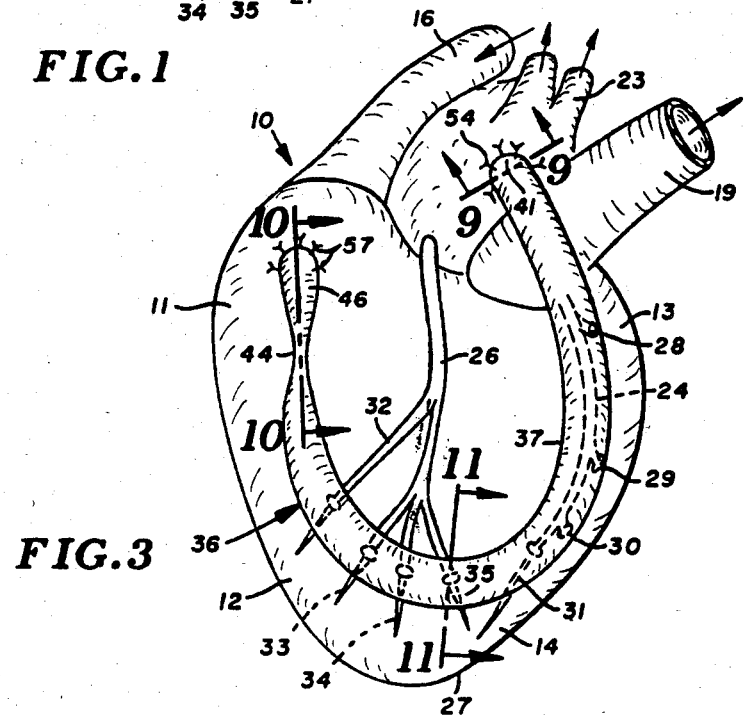
FIG. 3

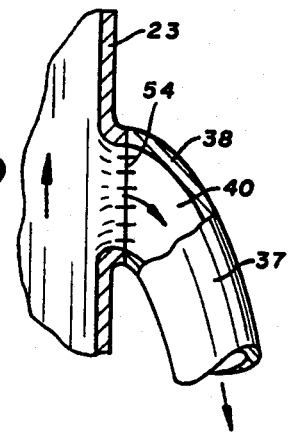
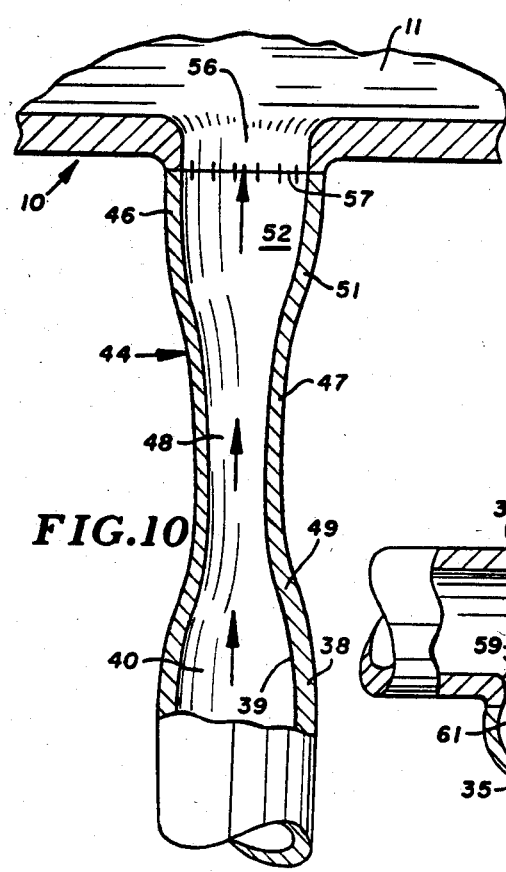
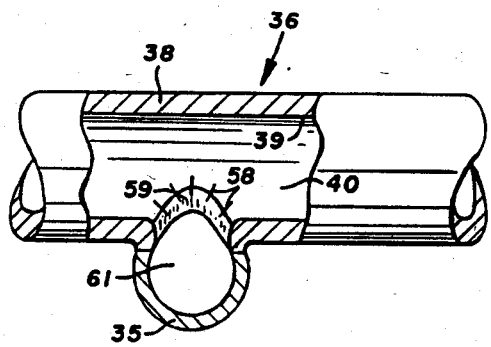

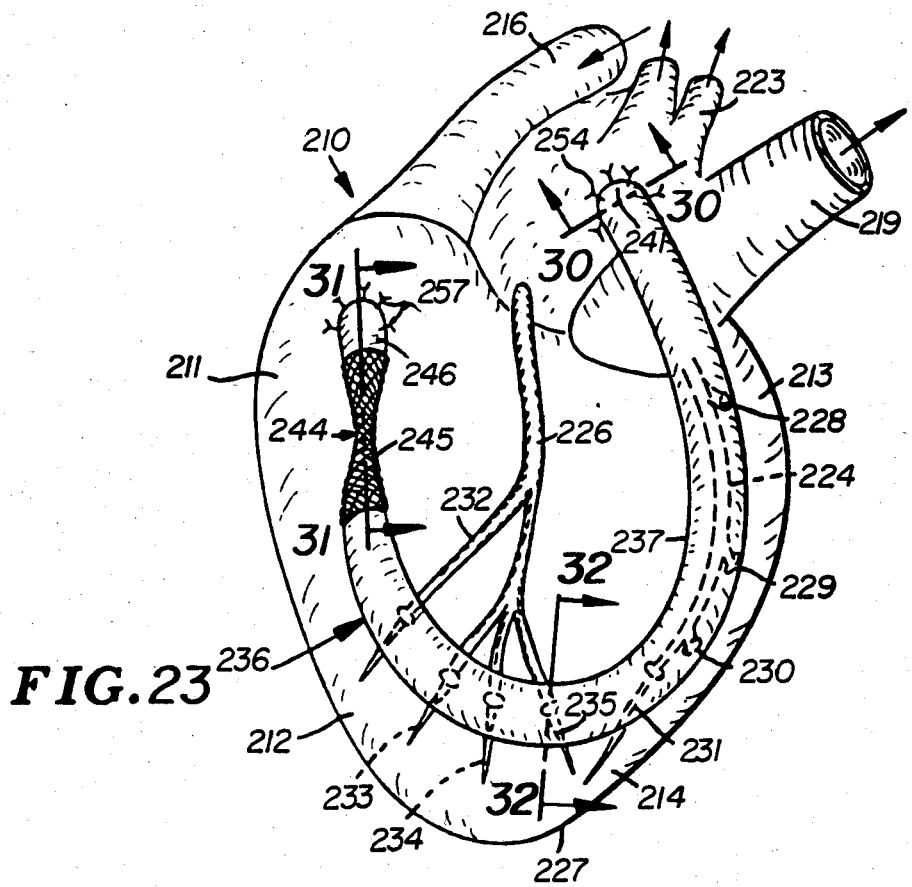

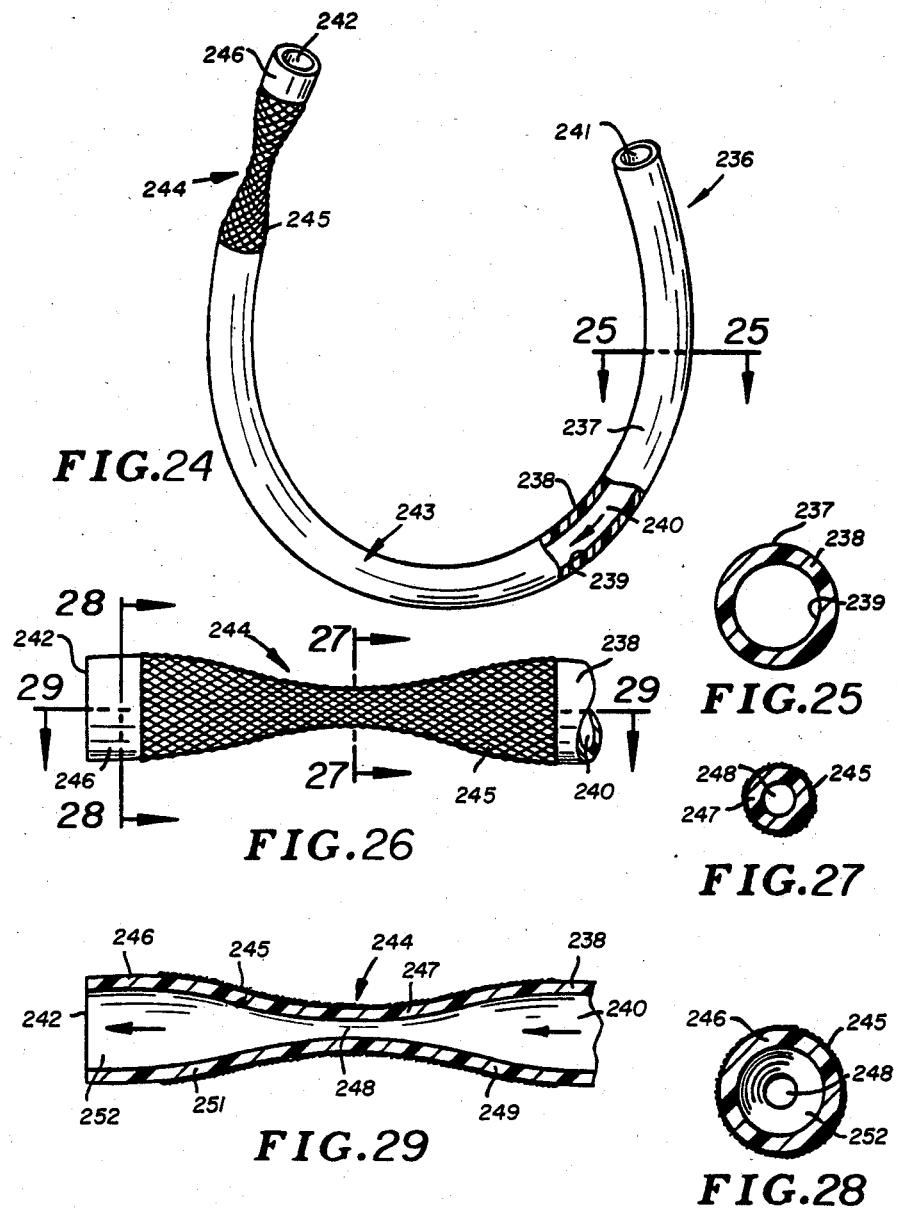

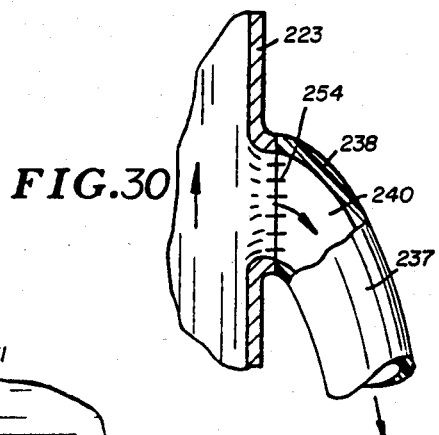
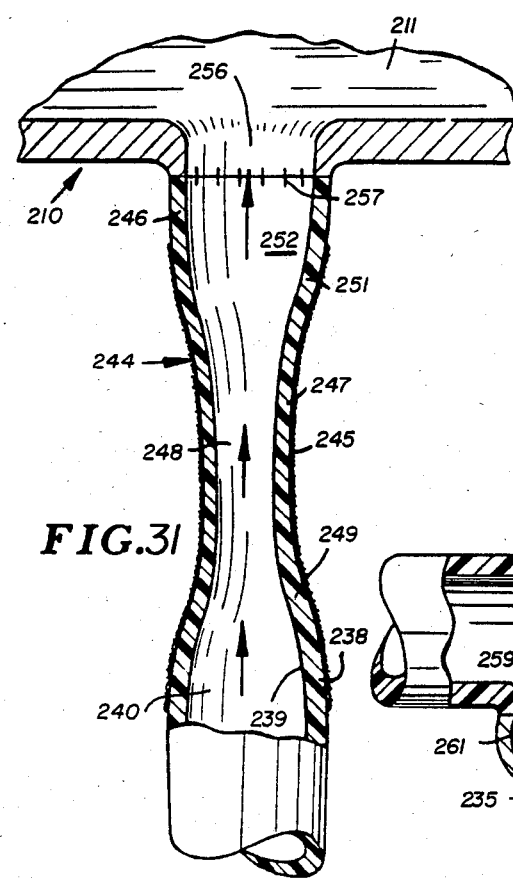
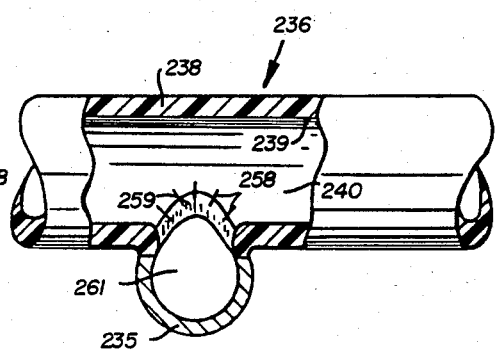

VASCULAR GRAFT AND BLOOD SUPPLY METHOD

This application is a continuation-in-part of Ser. No. 489,798 filed 4/29/83 now U.S. Pat. No. 4,562,597, which is a continuation-in-part of Ser. No. 448,955 filed 12/13/82 now U.S. Pat. No. 4,546,499.

FIELD OF INVENTION

The invention relates to implants used in the body to replace natural blood vessels to supply arterial blood to organs and tissues throughout the body. More particularly, the implants are vascular grafts used to supply blood to the tissue.

BACKGROUND OF INVENTION

Congenital defects, disease, or injury can render a person's blood vessels incapable of serving as an appropriate conduit for blood. Autogenous blood vessels may be relocated from their original site in the person's body and grafted to a new site as a replacement for the diseased or traumatized native vessel. Synthetic or non-autogenous tissue origin vascular grafts may also be implanted in a person to replace diseased or traumatized native vasculature.

Infection, aneurysm, thrombosis, hyperplastic tissue response, stenosis at the anastomoses, are all problems which occur with any known vascular graft whether it be of autogenous or non-autogenous origin. Long term patency of vascular grafts is dependent upon many factors including the skill of the implanting surgeon, patient health status, quality of the vascular graft and other factors. The influence of any particular factor on successful long term function has not been quantified. However, it is commonly held that low velocity of blood flow and low flow rate are major factors which reduce patency. Conversely then, higher flow rate and higher velocity of flow are major factors which increase patency longevity.

The autogenous saphenous vein is used successfully as a vascular conduit for coronary artery revascularization. Although the search for a suitable prosthetic graft for aortocoronary bypass continues, nothing better than the autogenous saphenous vein is available. Surgeons have been reluctant to use synthetic grafts in aortocoronary bypass because of few proved instances of long-term patency.

Although saphenous veins are used in aortocoronary bypass procedures, there are certain disadvantages: (1) unavailability, (2) small size, (3) non-uniform caliber, (4) varicosities, (5) large diameter, (6) sclerosis, (7) obstruction due to intimal hyperplasia, (8) aneurysm formation, (9) considerable time required for harvesting, (10) leg discomfort and swelling, and (11) possible leg infection.

A significant number of patients requiring aortocoronary bypass do not have suitable veins, or the veins have been used for previous aortocoronary bypass or for peripheral vascular bypass procedures. On occasion, the need for a graft may have been unforeseen prior to surgery, and the legs not prepared for harvesting of the vein. The cephalic vein from the arm has been used when the saphenous vein is not available. However, it is usually thin-walled and often of poor caliber. Furthermore, the cosmetic effect of harvesting the cephalic vein is unacceptable for some patients.

The internal mammary artery is widely accepted as suitable for myocardial revascularization, in that it has an excellent patency ratio, but is useful only for the left anterior descending and diagonal coronary arteries. Experience with free grafts of the internal mammary and radial arteries has been disappointing, since long-term patency has been poor.

The importance of the velocity of blood flow in autogenous vein grafts has been emphasized. There is evidence of an inverse relationship between the velocity of blood flow in venous grafts and the amount of intimal proliferation observed. Autopsy studies indicate that occlusion of aortocoronary saphenous vein grafts more than one month after operation is most commonly caused by fibrous intimal proliferation. Although the cause of this lesion has not been definitely established, studies would suggest that it is probably related to a low velocity of flow through the graft. This suggests that every effort should be made to achieve a high velocity of flow in coronary artery bypass grafts.

Synthetic vascular implants are disclosed by Liebig in U.S. Pat. Nos. 3,096,560; 3,805,301 and 3,945,052. These grafts are elongated knit fabric tubes made of yarn, such as polyester fiber. Dardik in U.S. Pat. No. 3,894,530 discloses the use of an umbilical cord for a vascular graft. Holman et al in U.S. Pat. No. 4,240,794 disclose a method of preparing human and other animal umbilical cords for use as a vascular replacement. The fabric tubes and umbilical cords have been used to replace the saphenous vein implant. The ends of the tubes and cords are anastomosed to ends of arteries to by-pass diseased areas of the arteries. They replace the diseased portions of the arteries.

SUMMARY OF INVENTION

The goal of vascular reconstructive surgery is to effectively supply blood to organs and tissues whose blood vessels integrity are compromised by congenital defects or acquired disorders, such as arteriosclerosis, trauma, and other diseases. The invention is a graft and a method employing the graft for supplying blood to organs and tissues throughout the body.

According to the invention, there is provided a graft for supplying blood to one or more blood receivers, such as blood vessels. The graft includes an elongated means having a continuous passage for carrying blood from a supply of blood under pressure to one or more blood receivers. The elongated means has a body providing a first passage for carrying of blood. The body has one or more openings and is connectable to at least one blood vessel for supplying blood to the opening to the blood vessel. The body has an inlet end means adapted to be connected to a supply of blood under pressure, whereby blood flows into the first passage and from the first passage into the blood vessel. The flow of blood and pressure of the blood in the first passage is controlled with a means having a restricted second passage connected to the distal portion of the body remote from the inlet end means. An outlet end means connects the means having the restricted second passage to blood receiving means. A pressure differential between the blood supply means and the blood receiving means maintains continuous and adequate blood flow at a desired pressure and velocity through the first and second passages and provides a continual supply of blood for the blood vessels that are attached to the body.

The graft is used to supply blood to one or more coronary artery branches in a primate heart. The heart has two atria for receiving blood from the vena cava and pulmonary veins and is connected to an aorta to carry blood under pressure from the heart. The graft comprises an elongated tubular means having a continuous longitudinal passage for carrying blood from the aorta to the atrium or a low pressure blood vessel. The tubular means has an inlet end anastomosed to the aorta so that blood under pressure flows from the aorta into the passage and is discharged through an outlet end into the atrium or other vessel of lower mean pressure than the aorta. The outlet end of the tubular means is anastomosed to the heart tissue around an opening in communication with the atrium. The tubular means has one or more openings used to provide blood to one or more coronary arteries or branches. The coronary arteries are sutured to the tubular means whereby blood flows through the openings in the tubular means into the coronary artery branches. The flow rate, velocity of flow, and pressure of the blood in the passage is controlled by a restriction located remote from the inlet end of the tubular means. The area of restriction is a restricted second passage having a diameter that is less than one-half the diameter of the main or first passage of the tubular means. The restricted passage is also smaller than the passage in the outlet end of the tubular means. The tubular means is generally U-shaped and encircles the critical areas of the heart beginning at the aorta and ending at either the right or left atrium or pulmonary artery. The pressure differential between the aorta and the atrium causes a continuous flow of blood in quantities and at velocities that inhibit thrombosis, and provides a continuous supply of blood at a desired pressure to the arteries connected to the tubular means.

In one embodiment of the invention, the tubular means is an elongated synthetic tube, such as a polytetrafluoroethylene tube, a Dacron tube, or a tube of other synthetic biocompatible material. The tube is continuous and has a reduced diameter section proximal to the distal or outlet end thereof. The reduced diameter section provides the restricted passage for controlling the blood flow and sustaining the pressure of the blood in the first passage of the tubular means. The restricted passage also controls the flow and velocity of blood moving through the outlet end of the tubular means.

A second embodiment of the invention utilizes a human umbilical cord or other tissue tubes of any origin as the elongated means. The umbilical cord can be linear or shaped to encircle the critical areas of the heart. The outlet or distal end portion of the cord has a reduced diameter to provide a restricted passage for the flow of blood through the cord. Selected arteries are anastomosed to the body of the cord and are provided with openings whereby blood from the lumen of the cord can flow into the arteries.

In a third embodiment of the invention, the elongated tubular means comprises an autogenous saphenous vein having a large enough caliber to assure adequate blood flow. The vein encircles the heart from the aorta and extends to the atrium. The distal or outlet end section of the vein accommodates an adjustable blood flow restrictor operable to reinforce the vein and reduce the cross sectional area of the vein passage to form a restricted passage. The restricted passage controls the flow of blood in the vein passage while maintaining a continuous flow of blood at a desired pressure. Selected portions of the vein are anastomosed to coronary arteries to provide continuous flow of blood to these arteries.

According to a fourth embodiment of the invention, there is provided a graft for supplying blood to one or more blood receivers, such as blood vessels. The graft includes an elongated tubular means having a continuous passage for carrying blood from a supply of blood under pressure to one or more blood vessels and blood receiver means. The flow of blood, velocity of blood flow, and pressure of the blood in the continuous passage is controlled with reinforced means having a restricted passage connected to the distal portion of the elongated tubular means remote from the inlet end means. The reinforced means maintains the cross sectional and longitudinal dimensions of the restricted passage over an extended period of time. The reinforcing means has an annular reinforcing sleeve surrounding the body to maintain the shape and size of the restricted passage. Other means can be used to reinforce the tubular means to ensure the shape and size of the restricted passage. The reinforcing means can be an increased wall thickness of the tubular means surrounding the restricted passage, or thread or tape surrounding the tubular means. An outlet end means connects the reinforced means having the restricted passage to blood receiving means. The outlet end means has an outlet passage larger than the restricted passage so as to reduce the velocity and pressure of the blood flowing into the atrium or low pressure blood vessel. A pressure differential between the blood supply means and the blood receiving means maintains continuous and adequate blood flow at a desired pressure through the passages and provides a continual supply of blood for the blood vessels that are attached to the elongated tubular means over a long period of time.

The elongated tubular means can be an autogenous blood vessel or a synthetic tube, such as a polytetrafluoroethylene tube, a Dacron tube, or a tube of other biocompatible material. The tube is continuous and has a reduced cross sectional area or throat section proximal to the distal or outlet end thereof. An elongated annular sleeve of reinforcing material surrounds the throat section to maintain the cross sectional area of the restricted passage through the throat section. The reinforcing material can be a fiber plastic. fiber mesh, a carbon tubular member, or metal tubular member attached to the outside of the throat section. The fiber can comprise a plurality of substantially non-elastic interconnected strands or wire-like members of metal, plastic, or carbon. The reinforcing material can be incorporated into the material of the throat section. The reinforcing material can be thread or tape wound around the throat section. A sleeve of rigid material, such as molded plastic, metal or carbon can be located about the throat section. The wall thickness of the throat section can be enlarged to provide for reinforcement thereof. The reduced cross sectional area provides a restricted passage for controlling the blood flow and sustaining the pressure of the blood in the first passage of the tubular means.

A fifth embodiment of the invention utilizes a human umbilical cord or autogenous blood vessel as the elongated means for carrying blood to the blood receiving vessels. The outlet or distal end of the cord has a reduced size to provide a restricted passage for controlling the flow, velocity and pressure of blood through the cord. The size of the restricted passage is maintained with an annular sleeve of reinforcing material mounted on the umbilical cord. The reinforcing material can be a fiber plastic, tape, a carbon tubular member, or metal tubular member surrounding a distal section of the umbilical cord. Selected arteries are anastomosed to the body of the cord and are provided with openings whereby blood from the lumen of the cord flows into the arteries.

The invention includes a method of providing a continuous supply of flowing blood at a desired pressure to one or more blood receiving vessels, such as coronary arteries of a primate. A graft having a blood flow restricting passage in the distal end section thereof is anastomosed to the aorta. The graft is placed adjacent the heart to locate portions thereof in proximity to selected coronary branch arteries. Selected portions of the graft are anastomosed to coronary arteries. The distal end of the graft is anastomosed to the atrium or low blood pressure section of the blood circulatory system. Blood under pressure continuously flows from the aorta into the graft, since there is a substantial blood pressure difference between the aorta and atrium. The restricted passage prevents the flow of blood from being excessive and maintains the blood pressure in the graft passage at substantially the same as the aorta blood pressure and controls the pressure and velocity of blood flowing from out of the graft to a low pressure vessel or atrium. The coronary arteries are perfused with sufficient quantities of blood.

IN THE DRAWINGS

FIG. 1 is an anterior view of a human heart;

FIG. 2 is a schematic longitudinal sectional diagram of the heart of FIG. 1;

FIG. 3 is an anterior view of a human heart having the graft of the invention;

FIG. 9 is an enlarged sectional view taken along the line 9—9 of FIG. 3;

FIG. 10 is an enlarged sectional view taken along the line 10—10 of FIG. 3;

FIG. 11 is an enlarged sectional view taken along the line 11—11 of FIG. 3;

FIG. 23 is an anterior view of a human heart having a reinforced vascular graft of the invention;

FIG. 24 is an enlarged partly sectioned plan view of the vascular graft of FIG. 23;

FIG. 25 is an enlarged sectional view taken along the line 25—25 of FIG. 24;

FIG. 26 is an enlarged distal end view of the vascular graft of FIG. 24;

FIG. 27 is an enlarged sectional view taken along the line 27—27 of FIG. 26;

FIG. 28 is an enlarged sectional view taken along the line 28—28 of FIG. 26;

FIG. 29 is an enlarged sectional view taken along the line 29—29 of FIG. 26;

FIG. 30 is an enlarged sectional view taken along the line 30—30 of FIG. 26;

FIG. 31 is an enlarged sectional view taken along the line 31—31 of FIG. 26; and FIG. 32 is an enlarged sectional view taken along the line 32—32 of FIG. 26.

DESCRIPTION OF PREFERRED EMBODIMENTS

Figure 4:
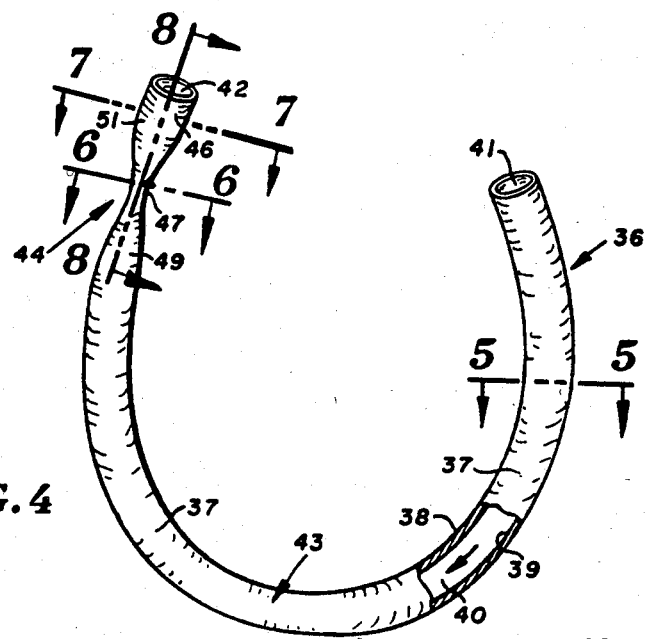
FIG. 4 is an enlarged partly sectioned plan view of the graft of FIG. 3.

Referring to FIGS. 1, 2 and 3, there is shown an anterior view of a human heart indicated generally at 10. Heart 10 has a right atrium 11, right ventricle 12, left atrium 13, and left ventricle 14. Blood from the body flows through vena cava 16 into right atrium 11. The pressure of the blood in right atrium 11 is low as the blood flows into atrium 11. A heart valve 17 controls the flow of blood from atrium 11 into right ventricle 12. The blood is pumped from right ventricle 12 through valve 18 into pulmonary artery 19, which is connected to the lungs. The blood returns from the lungs via the pulmonary vein 20 to left atrium 13. The blood flows from left atrium 13 through heart valve 21 into a left ventricle 14 and is pumped from the left ventricle 14 through valve 22 into aorta 23. The pressure differential of the blood between aorta 23 and the atrium 11 is approximately 90 mm Hg. The muscle tissue of the heart is provided with a supply of blood from two coronary arteries 24 and 26. Left coronary artery 24 extends from aorta 23 along the left side of the heart toward the apex 27. Coronary artery 24 has a number of branches 28, 29, 30 and 31, which supply blood to the muscle tissue. Left coronary artery 24 has a short common stem which bifurcates or trifurcates into branches 28-31. One branch 31, the anterior interventricular branch, moves downward to the anterior interventricular groove and rounds the acute margin of the heart just to the right of apex 27 and ascends a short distance up the posterior interventricular groove. Portions of the branch 31 anastomose with branches from the right coronary artery. These branches are very small in normal hearts. They may enlarge considerably in persons suffering from coronary arteriosclerosis in whom coronary arterial branches become obstructed or occluded. The right coronary artery 26 extends down the right side of the heart toward the apex or crux 27. Artery 26 has a number of branches 32, 33, 34 and 35, which feed blood to the heart tissue.

The right coronary artery 26 arises from the right anterior sinus of aorta 23 and runs along the right atrioventricular sulcus. It rounds the acute margin to reach the crux. It has a number of branches 32-35 to the anterior right ventricle wall. The right arterial branches of the right coronary artery 26 originate from the right coronary artery shortly after its take-off and ascends along the anteromedial wall of the right atrium. Variations of the branching pattern of the arteries 24 and 26 are common in the human heart. In about 67% of the cases, the right coronary artery 26 is dominant and supplies part of the left ventricle wall and ventricle septum. In 15% of the cases, the left coronary artery 19 is dominant and supplies all of the left ventricle and the ventricle septum, and part of the right ventricle wall, with blood. In about 18% of the cases, both coronary arteries 24 and 26 reach the crux 27. It is common for the first, second and third branches of the right coronary artery 26 to originate independently from the right sinus, rather than the parent artery. The graft of the invention can be used to provide an adequate supply of blood to these arteries.

Figure 5:
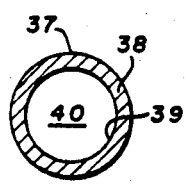
FIG. 5 is an enlarged sectional view taken along the line 5—5 of FIG. 4.
Figure 6:
FIG. 6 is an enlarged sectional view taken along the line 6—6 of FIG. 4.
Figure 7:
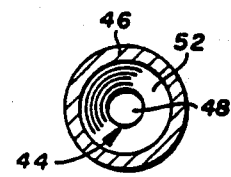
FIG. 7 is an enlarged sectional view taken along the line 7—7 of FIG. 4.
Figure 8:
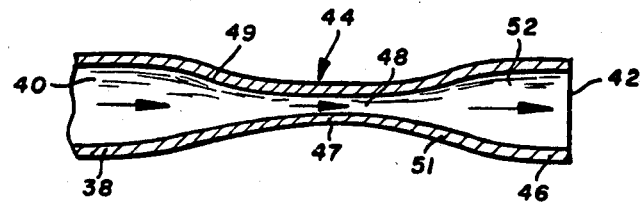
FIG. 8 is an enlarged sectional view taken along the line 8—8 of FIG. 4.
Figure 12:
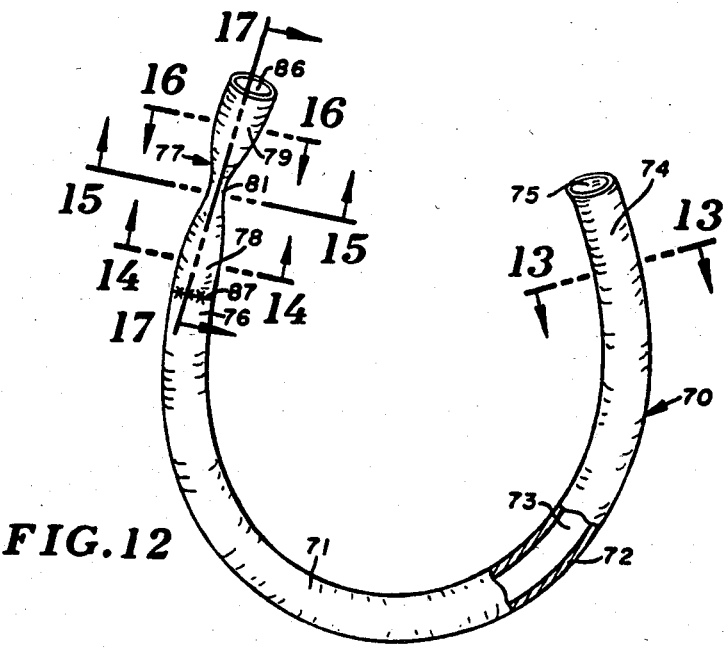
FIG. 12 is a plan view, partly sectioned, of a saphenous vein and distal and tubular blood flow restrictor anastomosed to the vein, usable as a graft of the invention.
Figure 13:
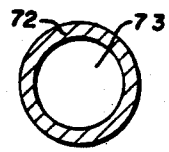
FIG. 13 is an enlarged sectional view taken along the line 13—13 of FIG. 12.
Figure 14:
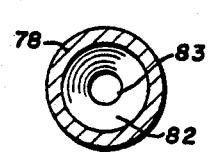
FIG. 14 is an enlarged sectional view taken along the line 14—14 of FIG. 12.
Figure 15:
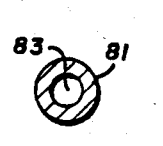
FIG. 15 is an enlarged sectional view taken along the line 15—15 of FIG. 12.
Figure 16:
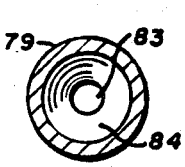
FIG. 16 is an enlarged sectional view taken along the line 16—16 of FIG. 12.
Figure 17:
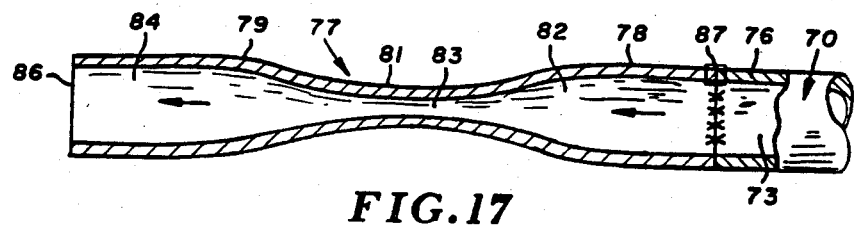
FIG. 17 is an enlarged sectional view taken along the line 17—17 of FIG. 12.
Figure 18:
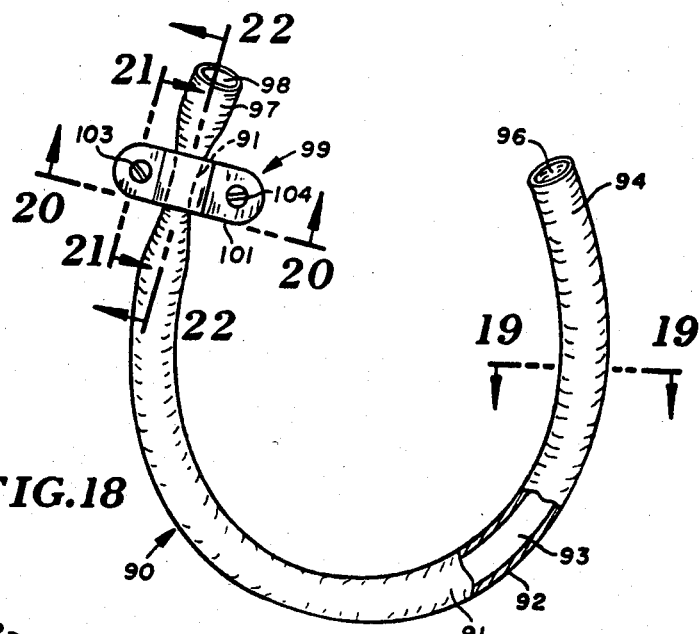
FIG. 18 is a plan view, partly sectioned, of a graft and adjustable blood flow restrictor therefor.
Figure 19:
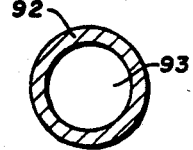
FIG. 19 is an enlarged sectional view taken along the line 19—19 of FIG. 1.
Figure 20:
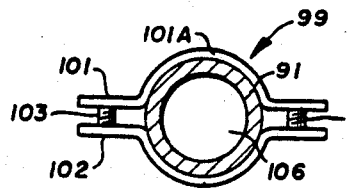
FIG. 20 is an enlarged sectional view taken along the line 20—20 of FIG. 18.
Figure 21:
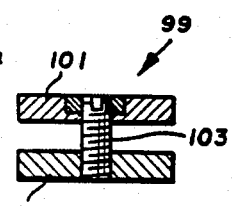
FIG. 21 is an enlarged sectional view taken along the line 21—21 of FIG. 18.

Referring to FIGS. 4-8, there is shown a vascular graft 36 of the invention indicated generally at 36. Graft 36 is an elongated member 37 having a generally U-shape and a continuous passage for carrying blood. Member 37 has a continuous cylindrical wall 38 having an inside surface 39 forming an elongated longitudinal passage 40. Tubular member 37 has a proximal aortic or inlet end 41 and a distal atrial or outlet end 42. A main generally U-shaped trunk 43 extends from inlet end 41 to a restricted or reduced diameter section 44. Restricted section 44 is connected to a distal end section 46. Preferably, restricted section 44 is about 2 to 5 cm from outlet end 42 when it is attached to the heart tissue. As shown in FIGS. 5-7, restricted section 44 has a cylindrical wall 47 integral with cylindrical wall 38 of the main trunk 43 and atrial end section 46. Wall 47 surrounds a throat passage 48 having a cross sectional area substantially smaller than the cross sectional area of passage 40. The cross sectional area of passage 40 is preferably more than four times larger than the cross sectional area of throat passage 48. Cylindrical wall 47 is joined to wall 38 with a converging conical wall portion 49 which directs the flow of blood into passage 48. The opposite ends of wall 47 are joined to a diverging conical wall portion 51 forming part of the atrial end sectional 46. Wall portion 51 surrounds an outlet passage 52 leading to the distal outlet end 42. The cross sectional area of outlet passage 52 is substantially the same as the cross sectional area of passage 40 of main trunk 43. The cross sectional area of outlet passage 52 can be larger than the cross sectional area of passage 40. Conical wall portions 49 and 51 each have a longitudinal length and an inside wall surface that has a gradual smooth taper to minimize turbulence in the blood flow. Preferably, cylindrical wall 47 surrounding passage 48 has a longitudinal length that is shorter than the longitudinal length of the wall portions 49 and 51. Other length and size relationships can be used. The longer the length of restriction section 44, the greater the blood pressure drop for a given cross sectional area of passage 48. Passage 52 provides a chamber wherein the velocity of the blood flow and blood pressure are decreased before it flows into the atrium of the heart. Distal end section 46 is of a size to permit easy attachment thereof to the heart tissue or blood receiving vessel.

The entire member 37 is a tubular structure, preferably made from a human umbilical cord. The umbilical cord can be pre-curved and tapered to form the desired restricted section 44 by processing. The tubular structure can be made from other tissue, including but not limited to a bovine carotid artery, an ovine subcutaneous mandrel grown tubular member, a feline esophagus and feline intestines. Other tubular structures, such as a polytetrafluoroethylene tube or other synthetic tube, can be used for vascular graft 36.

Referring to FIG. 3, vascular graft 36 is located adjacent the heart 10. Body 43 descends toward the midportion on the anterior surface of the heart and then encircles about to the posterior surface and ascends toward the right atrium. Restricted section 44 and atrial end section 46 are located adjacent atrium 11. As shown in FIG. 9, proximal or aortal end 41 of tubular member 37 is implanted into an aortic ostium 53 and anastomosed thereto with sutures 54. As shown in FIG. 10, the outlet or atrial end 46 is implanted into an ostium 56 in heart 10 open to atrium 11 and anastomosed thereto with sutures 57. The blood continuously flows through passage 40 of tubular member 37, by reason of the blood pressure difference between aorta 23 and atrium 11. Restricted passage 48 prevents the flow of blood through passage 40 from being excessive. The distal end section 46 of tubular member 37 can be anastomosed to the left atrium 13, whereby the blood flows from aorta 23 through passage 40 and tubular member 37 and into left atrium 13.

The body 43 of graft 36 is located adjacent one or more of the coronary branches 28-31 and 32-35. The surgeon has the option to anastomose and, therefore, perfuse one or more of the coronary branches along the path of the graft 36. Referring to FIG. 11, graft 36 is anastomosed to coronary branch 35 with sutures 58. The cylindrical wall 38 is provided with an opening 59 to allow blood to flow from passage 40 into the coronary artery passage 61. The restricted passage 48 adjacent the atrial end of the graft allows the coronary arteries to be perfused with sufficient quantities of blood at pressures within a few mm Hg of the aortic blood pressure. The flow of blood through restriction 48 is laminar and continues as a laminar flow through the passage 52 into atrium 11. There is a minimum of turbulence of the blood in graft 36. The interior surface 39 of the tubular member 37 is smooth and continuous. It does not have any nitrics which can stagnate and coagulate the blood.

An adequate flow of blood through the graft passage 40 is insured by the diameter of the aortic anastomosis 53 of approximately 2500 ml per minute. Tests indicate that, using a 5 mm diameter tubular graft with a simulated aortic flow of approximately 6000 ml per minute and pressure of 100 mm Hg, approximately 500 ml per minute will flow through a 2 mm restriction into the right atrium. Since the cardiac output is limited only by the venous return, the left ventricle will have an additional load of about 8 percent. Each coronary artery supplied with blood will require about 50 to 150 ml per minute of blood for adequate perfusion. Since the blood flow through an unrestricted 5 mm graft anastomosed to an aorta with blood flowing at 6000 ml per minute will provide blood flow well in excess of 2000 ml per minute, an adequate blood supply is available for up to 10 coronary branches, each carrying 150 mm per minute. Calculations of blood flow through the throat passage 48 show a Reynold's range of between 500 and 1000. The blood flow is laminar in passages 40 and 48.

In certain cases, a surgeon may choose to use the autogenous saphenous vein in lieu of synthetic graft 36 over the umbilical cord, as described herein. Referring to FIGS. 12-17, there is shown a segment of an autogenous saphenous vein indicated generally at 70 comprising an elongated member 71. Member 71 has a continuous cylindrical wall 72 surrounding a passage or lumen 73 for accommodating flowing blood. The inlet or proximal end 74 of member 71 has an opening 75. The saphenous vein 70 follows a path about the heart to reach occluded arteries in the manner of graft 36, as shown in FIG. 3. Lumen 73 has a generally uniform diameter from the inlet or aorta end 74 to the distal end 76.

A blood flow restrictor or tubular segment indicated generally at 77 is anastomosed to distal end 76 of vein 70. Blood flow restrictor 77 has an inlet end section 78 and an outlet end section 79 joined to an intermediate throat section 81. Section 78 has an inlet passage 82 longitudinally aligned with lumen 73. Inlet passage 82 communicates with a restricted passage 83 in throat section 81. Passage 83 opens to an outlet passage 84 in outlet end section 79. The cross sectional area of outlet passage 84 is substantially the same as the cross sectional area of the inlet passage 82. The size of restricted passage 83 can vary relative to the size of inlet passage 82. Preferably, the diameter of inlet passage 82 is more than twice the diameter of restricted passage 83. The cross sectional area of passage 82 is more than four times the cross sectional area of throat passage 83. Passage 83 allows blood to continuously flow through lumen 73 at a desired blood pressure in lumen 77 so that one or more coronary arteries can be perfused. The distal or atrial end section 79 has an open outlet 86 allowing blood to flow into the atrium of the heart when section 79 has been anastomosed to the atrium section of the heart.

In use, the surgeon harvests a section of the saphenous vein from the leg of the patient. A blood flow restrictor 77 having the desired size restricted passage 83 is secured with sutures 87 to distal end 76 of tubular member 71. The aortal end 74 is anastomosed to aorta 23. Tubular member 71 encircles the heart to locate atrium end 79 of restrictor 77 adjacent atrium 11. End 79 is anastomosed to the atrium section of the heart so that a continuous and adequate flow of blood is maintained through tubular member 70 and restrictor 77. The blood is at a desired pressure so that one or more coronary arteries can be perfused. The surgeon can anastomose one or more coronary arteries along the path of tubular member 70 in a manner, as shown in FIG. 11. This allows the continuous flow of blood under pressure from passage 73 into the lumen of the coronary arteries.

Referring to FIGS. 18-22, there is shown a tubular graft indicated generally at 90 usable to continuously supply blood to one or more coronary arteries of a human heart. Graft 90 has an elongated generally U-shaped member 91 having a continuous cylindrical wall 92. Wall 92 forms a generally uniform diameter passage 93. Member 91 has an aortic or proximal end 94 having an inlet opening 96 for receiving a continuous supply of blood from the aorta. The blood flows through passage 93 to a distal end 97 having an outlet opening 98. Distal end 97 is adapted to be anastomosed to the atrium section of the heart or a vein to receive blood therefrom.

Figure 22:
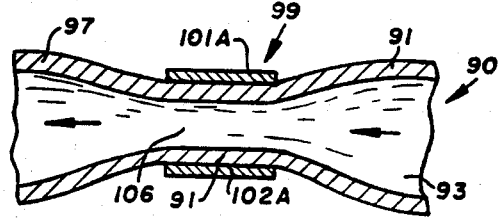
FIG. 22 is an enlarged sectional view taken along the line 22—22 of FIG. 18

As shown in FIGS. 18-22, an adjustable blood flow restrictor indicated generally at 99 is mounted on member 91 adjacent distal end 97 for restricting the flow of blood into distal end 97 while maintaining a continuous and adequate flow of blood at a desired pressure so that one or more coronary arteries can be perfused. Restrictor 99 also reinforces the tubular member forming the restricted passage. Blood flow restrictor 99 is a clamp unit having a first member 101 adjustably connected to a second member 102 with a pair of self-locking screws 103 and 104. Member 101 has an outwardly curved center section 101A located about an arcuate sector of member 91. Second member 102 has an oppositely outwardly curved center section 102A facing the curved center section 101A and engageable with an arcuate segment of member 91. Screws 103 and 104 are adjustable to move the first and second members 101 and 102 toward each other to adjust the size of the restricted passge 106, thereby adjusting the rate of flow of blood through passage 93 and adjusting the pressure of the blood in passage 93. A cylindrical mandrel having a desired cross sectional area is used to provide the restricted passage with a desired size or cross sectional area. The mandrel is inserted into the distal end section of member 91. Restrictor 99 is placed over the distal end section and clamped onto member 91. The curved center sections 101A and 102A move toward each other and force the wall of the member about the mandrel. This mandrel is then removed from the member 91. Restrictor 99 maintains the selected cross section of passage 106, as shown in FIG. 22.

Referring to FIG. 23, there is shown an anterior view of a human heart indicated generally at 210. Heart 210 has a right atrium 211, right ventricle 212, left atrium 213, and left ventricle 214. Blood from the body flows through vena cava 216 into right atrium 211. The pressure of the blood in right atrium 211 is low as the blood flows into atrium 211. A heart valve controls the flow of blood from atrium 211 into right ventricle 212. The blood is pumped from right ventricle 212 through a valve into pulmonary blood returns from the lungs via the pulmonary vein to left atrium 213. The blood flows from left atrium 213 through the heart valve into a left ventricle 214 and is pumped from the left ventricle 214 through the valve into aorta 223. The muscle tissue of the heart is provided with a supply of blood from two coronary arteries 224 and 226. Left coronary artery 224 extends from aorta 223 along the left side of the heart toward apex 227. Coronary artery 224 has a number of branches 228, 229, 230 and 231, which supply blood to the muscle tissue. Left coronary artery 224 has a short common stem which bifurcates or trifurcates into branches 228-231. One branch 231, the anterior interventricular branch, moves downward to the anterior interventricular groove and rounds the acute margin of the heart just to the right of apex 227 and ascends a short distance up the posterior interventricular groove. Portions of branch 231 anastomose with branches from the right coronary artery. These branches are very small in normal hearts. The may enlarge considerably in persons suffering from coronary arteriosclerosis in whom coronary arterial branches become obstructed or occluded. The right coronary artery 226 extends down the right side of the heart toward apex or crux 227. Artery 226 has a number of branches 232, 233, 234 and 235, which feed blood to the heart tissue.

Referring to FIGS. 24-28, there is shown a reinforced vascular graft of the invention indicated generally at 236. Graft 236 is an elongated tubular member 237 having a generally U-shape and a continuous passage 240 for carrying blood. Member 237 has a continuous cylindrical wall 238 having an inside surface 239 forming elongated longitudinal passage 240. Tubular member 237 has a proximal aortic or inlet end 241 and a distal atrial or outlet end 242. A main trunk 243 extends from inlet end 241 to a restricted or reduced section indicated generally by member 244. Restricted section 244 is connected to a distal end section 246. Preferably, restricted section 244 is about 2 to 5 cm from outlet end 242 when it is attached to the heart tissue. As shown in FIGS. 25-27, restricted section 244 has a cylindrical wall 247 integral with cylindrical wall 238 of main trunk 243 and atrial end section 246. Wall 247 surrounds a restricted passage 248 having a cross sectional area substantially smaller than the cross sectional area of passage 240. The cross sectional area of passage 240 is preferably more than four times larger than the cross sectional area of restricted passage 248. Cylindrical wall 247 is joined to wall 238 with a converging conical wall portion 249 which directs the flow of blood into passage 248. The opposite ends of wall 247 are joined to a diverging conical wall portion 251 forming part of the atrial end section 246. Wall portion 251 surrounds an outlet passage 252 leading to the distal outlet end 242. The cross sectional area of outlet passage 252 is substantially the same as the cross sectional area of passage 240 of main trunk 243. Conical wall portions 249 and 251 each have a longitudinal length and an inside wall surface that has a gradual smooth taper to minimize turbulence in the blood flow. Preferably, cylindrical wall 247 surrounding passage 248 has a longitudinal length that is shorter than the longitudinal length of the wall portions 249 and 251. Other length and size relationships can be used. The longer the length of restricted section 244, the greater the blood pressure drop for a given cross sectional area of passage 248. Passage 252 provides a chamber wherein the velocity of the blood flow is decreased before it flows into the atrium of the heart. Distal end section 246 is of a size to permit easy attachment thereof to the heart tissue or blood receiving vessel.

Vascular graft 236 is an elongated tube of synthetic material that is biologically inert and does not deteriorate in the body over an extended period of time. Examples of suitable materials are Polytetrafluoroethylene and Dacron plastics. Other materials and combinations of materials can be used for vascular graft 236. The restricted section 244 is reinforced with a sleeve 245 to insure that the cross sectional area and length of passage 248 is maintained over a long period of time. The material of wall 247 does not expand in use when reinforced with sleeve 245 whereby the size and length of passage 248 is kept substantially constant during use of vascular graft 236. Sleeve 245 is a reinforcing structure for wall 247 to inhibit its dilation or expansion, contraction, and elongation so as to maintain desired dimensions of passage 248 over an extended period of time. This insures continuous and controlled flow of blood through vascular graft 236 and maintains the pressure of blood in passage 240 at a level to perfuse the coronary branches attached to trunk 38. Sleeve 245 can be a tubular fiber member of metal, plastic, or carbon fibers formed into a mesh surrounding restricted section 244. Tape and thread can be used to form sleeve 245. Sleeve 245 can be bonded or otherwise secured to the outer surface of restricted section 244. Reinforcing structure can be incorporated into the material of restricted section 244. The thickness of the wall of the restricted section can be increased to strengthen the restricted section. The sleeve can be a rigid plastic carbon or metal tubular member located about the restricted section.

As shown in FIGS. 24, 26, 29 and 31, sleeve 245 surrounds wall 247 and conical wall portions 249 and 251 joined to wall 247. Sleeve 245 is continuous from conical wall portion 249 to conical wall portion 251 so as to reinforce both converging and diverging portions of the walls forming the restricted passage 248.

The entire vascular graft 236 can be a tubular structure, made from a human umbilical cord. The umbilical cord is cured and tapered to form the desired restricted section 244. The restricted section is reinforced with mechanical reinforcing means as described herein. Other types of blood vessels and tissue tubes provided with a reinforced restricted section can be used as the graft.

Referring to FIG. 23, vascular graft 236 is located adjacent heart 210. Body 243 descends toward the midportion on the anterior surface of the heart and then encircles about to the posterior surface and ascends toward the right atrium. Restricted section 244 and atrial end section 246 are located adjacent atrium 211. As shown in FIG. 30, proximal or aortal end 241 of tubular member 237 is implanted into an aortic ostium 253 and anastomosed thereto with sutures 254. As shown in FIG. 31, the outlet or atrial end 246 is attached to the heart 30 around ostium 256 open to atrium 211 and anastomosed thereto with sutures 257. The blood continuously flows through passage 240 of tubular member 237, since the blood pressure difference between aorta 223 and atrium 211 is about 90 mm Hg. Restricted passage 248 prevents the flow of blood through passage 240 from being excessive. Restricted section 244 reinforced with sleeve 245 maintains a controlled flow of blood through passage 248. The cross sectional area and length of passage 248 is retained during prolonged use by the reinforcing sleeve 245 in cooperation with wall 247. The distal end section 246 of tubular member 237 can be anastomosed to left atrium 213, whereby the blood flows from aorta 223 through passages 240, 248 and 252 and into left atrium 213.

The body 243 of vascular graft 236 is located adjacent one or more of the coronary branches 228 to 231 and 232 to 235. The surgeon has the option to anastomose and, therefore, perfuse one or more of the coronary branches along the path of vascular graft 236. Referring to FIG. 31, vascular graft 236 is anastomosed to coronary branch 235 with sutures 258. The cylindrical wall 238 is provided with an opening 259 to allow blood to flow from passage 240 into the coronary artery passage 261. The restricted passage 248 adjacent the atrial end of the vascular graft allows the coronary arteries to be perfused with sufficient quantities of blood at pressures within a few mm Hg of the aortic blood pressure. The flow of blood through restriction 248 is laminar and continues as a laminar flow through the passage 252 into atrium 211. The outlet end passage 252 being larger than the restricted passage 248 reduces the pressure of the blood and velocity of the blood before it flows into atrium 211. There is a minimum of turbulence of the blood in graft 236. The interior surface 239 of the tubular member 237 is smooth and continuous. It does not have any nitrics which can stagnate and coagulate the blood.

The grafts of the invention can be used to carry blood in peripheral revascularization procedures of the lower extremities. For example, the graft would be interposed between the most distal arterial anastomosis and the popliteal vein or one of its major branches. The source of blood would be the femoral artery and the anastomosis would be made in the popliteal artery and/or its distal branches, the anterior tibia, posterior tibia, or peroneal arteries. The blood flow restricting passage or throat passage located between these arteries and the distal end of the graft controls the blood flow through the graft. The control of blood flow allows adequate perfusion of blood pressure to these arteries and at the same time insures continuous blood flow to maintain patency of the graft.

While there has been shown and described the preferred embodiments of the graft of the invention, and method of supplying a continuous blood flow to one or more arteries, it is understood that changes in the materials, size, length of the graft, and location of the graft may be made by those skilled in the art without departing from the invention. The invention is defined in the following claims.

We claim:

1. A graft for supplying blood to one or more coronary arteries of a primate heart having a right atrium, pulmonary artery, and an aorta joined to the heart to receive blood therefrom comprising: an elongated biocompatible means having a cylindrical wall having an inside cylindrical surface surrounding a continuous passage for carrying blood, said means having an inlet end attachable to the aorta whereby blood under pressure flows from the aorta into said passage, and an outlet end attachable to the heart to discharge blood into the right atrium, said wall being provided with one or more openings and being attachable to one or more coronary arteries whereby blood flows from said passage through said openings into one or more of said coronary arteries, and means for restricting the flow of blood and sustaining the pressure of the blood in said passage located remote from the inlet end and between the outlet end and said openings thereby maintaining a continuous flowing supply of blood to said coronary arteries and into the right atrium, said means for restricting the flow of blood in said passage comprises a section of said cylindrical wall having an inside cross sectional area smaller than the cross sectional area of said passage thereby providing said passage with a throat, said cylindrical wall having an outlet end portion connected to said section, said outlet end portion having an outlet passage for carrying blood from the throat to the atrium, said outlet passage having a cross sectional area larger than the cross sectional area of the throat.

2. The graft of claim 1 wherein: said elongated means has a generally U-shaped tubular body.

3. The graft of claim 1 wherein: said elongated means and means for restricting the flow of blood comprises a synthetic tube.

4. The graft of claim 1 wherein: said elongated means and means for restricting the flow of blood comprises an umbilical cord.

5. The graft of claim 4 wherein: the umbilical cord has a distal end section, said distal end section having a throat passage smaller in size than the passage in the elongated means to sustain the pressure of the blood in the passage of the elongated means and restrict the amount of blood that flows through said passage in the elongated means.

6. The graft of claim 5 wherein: said throat passage is spaced upstream from the distal end of the umbilical cord.

7. The graft of claim 4 including means located about a distal end section of the cord for reducing the cross sectional area of the passage of the cord to restrict the amount of blood that flows through said passage of the cord.

8. The graft of claim 7 wherein: the means located about a distal end section of the cord comprises clamp means engageable with the cord.

9. The graft of claim 8 wherein: said clamp means includes means for adjusting the cross sectional area of the throat passage.

10. The graft of claim 1 wherein: said elongated means is saphenous vein, and the means for restricting the flow of blood is attached to the outlet end of the saphenous vein.

11. The graft of claim 10 wherein: said means for restricting the flow of blood comprises tubular means having a throat passage with a cross sectional area smaller than the cross sectional area of the passage of the saphenous vein to restrict the flow of blood therein.

12. The graft of claim 11 wherein: the cross sectional area of the throat passage is less than one-half of the cross sectional area of the passage of the saphenous vein.

13. The graft of claim 1 wherein: said inside cylindrical surface has a generally uniform diameter.

14. The graft of claim 1 wherein: said outlet end portion has a length of less than 10 cm.

15. The graft of claim 1 wherein: said cylindrical wall has a generally U-shape.

16. The graft of claim 1 wherein: said passage has a diameter of about 5 mm and the throat has a diameter of about 2 mm.

17. The graft of claim 1 wherein: said throat has a cross sectional area that is less than one-half the cross sectional area of the passage.

18. A graft for supplying blood to one or more coronary arteries of a primate heart having a right atrium, pulmonary artery, and an aorta joined to the heart to receive blood therefrom comprising: an elongated biocompatible means having a continuous passage for carrying blood, said means having an inlet end attachable to the aorta whereby blood under pressure flows from the aorta into said passage, and an outlet end attachable to the heart to discharge blood into the right atrium, said means being provided with one or more openings and being attachable to one or more coronary arteries whereby blood flows from said passage through said openings into one or more of said coronary arteries, and means for restricting the flow of blood and sustaining the pressure of the blood in said passage located remote from the inlet end and between the outlet end and said openings thereby maintaining a continuous flowing supply the blood to said coronary arteries and into the right atrium, and means for reinforcing the means for restricting the flow of blood to maintain the size and shape thereof.

19. The graft of claim 18 wherein: said means for reinforcing the means for restricting the flow of blood comprises an annular sleeve.

20. The graft of claim 19 wherein: the sleeve comprises fiber means providing a reinforcement.

21. The graft of claim 20 wherein: the fiber means comprise a plurality of substantially non-elastic strands.

22. The graft of claim 1 wherein: said means for restricting the flow of blood comprises tubular means having converging, linear, and diverging tubular sections providing a restricted passage with a decreasing cross sectional area, a cross sectional area smaller than the cross sectional area of the continuous passage and an increasing cross sectional area to restrict the flow of blood through the restricted passage.

23. the graft of claim 22 wherein: said elongated means and means for restricting the flow of blood comprises a synthetic tube having a restricted section providing a restricted passage.

24. The graft of claim 22 wherein: said elongated means, and means for restricting the flow of blood comprises an unbilical cord having a restricted section providing a restricted passage.

25. The graft of claim 18 wherein: said means for restricting the flow of blood and sustaining the pressure of the blood in said passage comprises a tubular wall joined to a converging wall and a diverging wall providing a restricted passage having a decreasing cross sectional area, a cross sectional area smaller than the continous passage, and an increasing cross sectional area, said means for reinforcing the means for restricting the flow of blood comprising a tubular sleeve surrounding and mounted on the tubular wall, converging wall, and diverging wall.

26. The graft of claim 1 wherein: said elongated means comprises a synthetic tube having a restricted section providing a restricted passage, said restricted section having enlarged wall thickness to reinforce the restricted section.

27. A graft for supplying blood to one or more blood vessels comprising: a tubular body having an inlet end adapted to be connected to means providing a supply of blood under pressure, said tubular body having a first passage open to the inlet end adapted to be provided with one or more openings which are connected to at least one blood vessel for supplying blood to said vessel, said tubular body also having a restricted second passage and an outlet end joined to said body remote from said inlet end said restricted second passage being between said one or more openings and said outlet end and acting to control the flow of blood through the first passage and sustain the pressure of blood in the first passage in order to continuously supply blood to said vessel, said outlet end having a third passage with a cross sectional area larger than the cross sectional area of said restricted second passage said third passage being open to the restricted second passage adapted to be connected to a receiver of blood having blood pressure lower than the pressure of the supply of blood thereby maintaining a continuous supply of blood to said vessel and a continuous flow of blood through said first passage, second passage and third passage into the receiver of blood.

28. The graft of claim 27 wherein: said body has a generally U-shape.

29. The graft of claim 27 wherein: said body means having a restricted second passage and an outlet end comprise a synthetic tube.

30. The graft of claim 27 wherein: said body means having a restricted second passage and an outlet, and said body including an umbilical cord.

31. The graft of claim 27 wherein: said body is a saphenous vein, and the means for controlling the flow of blood through the first passage is attached to the outlet end of the saphenous vein.

32. The graft of claim 31 wherein: said means for controlling the flow of blood comprises a body having said restricted second passage, and means connectable to the saphenous vein.

33. The graft of claim 27 wherein: said means having a restricted second passage is located adjacent said outlet end.

34. The graft of claim 33 wherein: said means having a restricted second passage is located within 10 cm of said outlet end.

35. The graft of claim 27 wherein: said means having a restricted second passage includes clamp means located about a distal section of said body for reducing the size of said distal section thereby providing said second passage.

36. The graft of claim 35 wherein: said clamp means includes means for adjusting the clamp means to vary the size of said distal section thereby adjusting the size of said second passage.

37. The graft of claim 27 wherein: said second passage has a cross sectional area that is less than one-half the cross sectional area of the first passage.

38. A graft for supplying blood to one or more blood vessels comprising: a tubular body having an inlet end adapted to be connected to means providing a supply of blood under pressure, said tubular body having a first passage open to the inlet end adapted to be provided with one or more openings and connected to at least one blood vessel for supplying blood to said vessel, means having a restricted second passage and an outlet end joined to said body remote from said inlet end between said one or more openings and said outlet end to control the flow of blood through the first passage and sustained the pressure of the blood in the first passage to continuously supply blood to said vessel, said outlet end open to the restricted second passage adapted to be connected to a receiver of blood having blood pressure lower than the supply of blood thereby maintaining a continuous supply of blood to said vessel and flow of blood through said first and second passages into the receiver of blood, and reinforcing means cooperating with the means having a restricted second passage to maintain the size and shape of said restricted second passage.

39. The graft of claim 38 wherein: the reinforcing means comprises a sleeve located about said means having a restricted second passage.

40. The graft of claim 38 wherein: the means having a restricted passage comprises a tubular wall joined to a converging wall and a diverging wall, said restricted passage being a continuation of the first passage, said restricted passage having a decreasing cross sectionsl area, a cross sectional area smaller than the continuous passage, and an increasing cross sectional area, said reinforcing means comprising a sleeve surrounding and mounted on the tubular wall, converging wall, and diverging wall.

41. The graft of claim 38 wherein: the means having a restricted passage comprises a synthetic tube, said reinforcing means including enlarged wall thickness of said tube to maintain the size and shape of said restricted passage.

42. A graft for supplying blood to one or more blood vessels comprising: an elongated tubular means for carrying blood from a supply of blood under pressure to one or more blood vessels, said tubular means having body means providing a first passage for carrying blood, said body means being provided with one or more openings which are connectible to at least one blood vessel for supplying blood through said opening to said blood vessel, said tubular means also having inlet end means adapted to be connected to the supply of blood under pressure whereby blood flows into said first passage and from said first passage into said blood vessel, means having a restricted second passage joined to said body means remote from said inlet end means to control the flow of blood through the first passage and sustaining the pressure of the blood in the first passage, and an outlet end means having a third passage larger than said second passage joined to the means having the restricted second passage adapted to be connected to means for receiving blood having blood pressure lower than the pressure of the supply of blood whereby blood continuously flows to said blood vessel and continuously flows through the first passage, second passage and third passage into the means for receiving blood.

43. The graft of claim 42 wherein: said body means has a U-shape.

44. The graft of claim 42 wherein: said elongated means is a synthetic tube.

45. The graft of claim 42 wherein: said elongated means is an umbilical cord.

46. The graft of claim 42 wherein: said body means and inlet end means comprises a saphenous vein, and said means having a restricted second passage comprises a tubular member having said second passage, and means connectable to said saphenous vein.

47. The graft of claim 42 wherein: said means having a restricted second passage includes clamp means located about a distal section thereby adjusting the size of said second passage.

48. The graft of claim 47 wherein: said clamp means includes means for adjusting the clamp means to vary the size of said distal section thereby adjusting the size of said second passage.

49. A graft for supplying blood to one or more blood vessels comprising: an elongated tubular means for carrying blood from a supply of blood under pressure to one or more blood vessels, said tubular means having body means providing a first passage for carrying blood, said body means provided with one or more openings and connectible to at least one blood vessel for supplying blood through said one opening to said blood vessel, inlet end means adapted to be connected to the supply of blood under pressure whereby blood flows into said first passage and from said first passage into said blood vessel, means having a restricted second passage joined to said body means remote from said inlet end means to control the flow of blood through said first passage and to sustain the pressure of blood in the first passage, an outlet end means having a third passage joined to the means having the restricted second passage adapted to be connected to means for receiving blood having blood pressure lower than the pressure of the supply of blood whereby the blood continuously flows through said blood vessel and into the means for receiving blood, and reinforcing means cooperating with the means having a restricted second passage to maintain the size and shape of said restricted second passage.

50. The graft of claim 49 wherein: the reinforcing means comprises a sleeve located about said means having a restricted second passage.

51. The graft of claim 49 wherein: the means having a restricted passage comprises a synthetic tube, said reinforcing means including an enlarged wall thickness of said tube to maintain the size and shape of said restricted passage.

52. The graft of claim 42 wherein: the means having a restricted second passage has a tubular wall surrounding said restricted passage, said restricted passage having a cross section smaller than said first passage, a converging wall joining the inlet of the tubular wall to the body means, and a diverging wall joining the outlet of the tubular wall to said outlet end means.

53. The graft of claim 52 wherein: said third passage of the outlet end means has a cross section larger than the cross section of the restricted passage.

54. The graft of claim 52 including: tabular sleeve means surrounding the tubular wall, converging wall, and diverging wall to reinforce said walls and maintain the cross sectional size of the restricted passage.

55. A graft for supplying blood to one or more blood vessels comprising: a tubular body having an inlet end adapted to be connected to means providing a supply of blood under pressure, said tubular body having a first passage open to the inlet end adapted to be provided with one or more openings and connected to at least one blood vessel for supplying blood to said vessel, means having a restricted second passage and an outlet end joined to said body remote from said inlet end between said one or more openings and said outlet end to control the flow of blood through the first passage and sustain the pressure of blood in the first passage to continuously supply blood to said vessel, said outlet end open to the restricted second passage adapted to be connected to a receiver of blood having blood pressure lower than the supply of blood thereby maintaining a continuous supply of blood to said vessel and flow of blood through said first passage and said second passage into the receiver of blood, and means having a restricted second passage comprises an outlet end section of the tubular body, said end section having a tubular wall surrounding a restricted passage smaller in cross sectional area than said first passage, a converging wall joining the inlet of the tubular wall to said body, and a diverging wall joined to the outlet of the tubular wall.

56. The graft of claim 55 including: tubular sleeve means surrounding the tubular wall, converging wall, and diverging wall to reinforce said walls and maintain the cross sectional size of the restricted passage.

57. The graft of claim 1 wherein: said outlet end portion has a tubular wall surrounding said throat, a converging wall joined to the inlet of the tubular wall, and a diverging wall joined to the outlet end of the tubular wall, said outlet end portion having a tubular member joined to said diverging wall.

58. The graft of claim 57 including: tubular sleeve means surrounding the tubular wall, converging wall, and diverging wall to reinforce said walls and maintain the cross sectional size of the restricted passage.

59. A graft for supplying blood to one or more coronary arteries of a primate heart having a right atrium, and an aorta joined to the heart to receive blood therefrom comprising: a single elongated tubular member having a single passage, an inlet end attachable to the aorta whereby blood under pressure flows from the aorta into said passage, an outlet end attachable to the heart to direct blood into the right atrium, said tubular member having one or more openings and being attachable to one or more coronary arteries to align the opening with said arteries whereby blood flows from said passage through said openings into one or more of said coronary arteries, said tubular member having a restricted section between said openings and the outlet end, said section having a tubular wall surrounding a restricted passage small in cross section than said single passage, a converging annular wall on the inlet side of the tubular wall, and a diverging annular wall on the outlet side of the tubular wall, said converging wall providing a passage decreasing in cross sectional area to the restricted passage, and said diverging annular wall providing a passage increasing in cross sectional area from the restricted passage, said restricted passage limiting the flow of blood and sustaining the pressure of the blood in said single passage to maintain continuous flow of blood in said single passage to perfuse said coronary arteries and discharge blood to the right atrium.

60. The graft of claim 59 including: sleeve means surrounding the tubular wall, converging wall, and diverging wall to reinforce said walls and maintain the cross sectional size of the restricted passage.

61. The graft of claim 59 including: an end tubular section joined to the diverging wall, said tubular section having a passage with a cross sectional larger than the cross sectional area of the restricted passage.

* * * * *

UNITED STATES PATENT AND TRADEMARK OFFICE
CERTIFICATE OF CORRECTION

PATENT NO. : 4,601,718

DATED : July 22, 1986

INVENTOR(S) : Zinon C. Possis et al.

It is certified that error appears in the above-identified patent and that said Letters Patent is hereby corrected as shown below:

Column 10, line 12, "passge" should read -- passage --.

Column 10, line 53, The" should resd -- They --.

Column 18, line 9, "tabular" should read -- tubular --.

Signed and Sealed this

Third Day of March, 1987

Attest:

DONALD J. QUIGG

Attesting Officer

Commissioner of Patents and Trademarks